United States Patent [19]

Yoshida

[11] Patent Number: Plant 7,742

[45] Date of Patent: Dec. 10, 1991

[54] AFRICAN VIOLET NAMED 'KRISTIN'

[76] Inventor: Eiichi Yoshida, P.O. Box 4836, Hayward, Calif. 94540-4836

[21] Appl. No.: 524,124

[22] Filed: May 14, 1990

[51] Int. Cl.[5] ..... A01H 5/00

[52] U.S. Cl. ..... Plt./69

[58] Field of Search ..... Plt./69

*Primary Examiner*—James R. Feyrer

[57] ABSTRACT

A new variety of African violet plant for potted plant culture particularly distinguished by its year 'round blooming capability, its profuse production of long-lasting flowers, and its compact growth with abundant foliage of solid green color which provides a spreading base and attractive backing for the heavy clusters of blossoms.

1 Drawing Sheet

BACKGROUND OF THE NEW PLANT

This new variety of African violet plant was obtained by cross-pollenating the seed parent "Melodie" Rhonda and the pollen parent *S. shumensis*×S."Optimara" Georgia. The seed pods of the pollenated plants were used as the generic basis for initiating further propagation trials. The specified plant was a selection from among the initial seventy-three selected plants remaining from the initial cross. The plant of this disclosure was selected based on a number of outstanding characteristics in combination which included attractive, balanced plant confirmation with starkly contrasting top and bottom leaf coloration with leaves of uniform shape and which are gently upwardly cupped. The plant further displays a generous number of and central placement of flowers of single and attractive, rounded shape with slightly ruffled petal outer portions, moderately deep pink petals which appealingly contrast with bright yellow, conspicuous anthers. Flowers are moderately compactly placed on strong peduncles generally above the strong petioles of the oldest leaves.

This selection was subsequently denominated 'Kristin'. I have asexually reproduced 'Kristin' by taking leaf cuttings to start plants in the conventional manner for *Saintpaulia ionantha.* Clones of this original selection have proven to be substantially identical to the parent plant in all distinguishing characteristics to establish that 'Kristin' is genetically stable.

BRIEF DESCRIPTION OF THE DRAWING

Sheet one is a full color photographic view of the plant in bloom, the colors shown being as nearly true as it is reasonably possible to obtain by conventional photographic procedures.

DESCRIPTION OF THE PLANT

The following is a detailed description of my new African violet plant with the color designation being accorded to the R.H.S. Colour Chart published by the Royal Horticultural Society of London, England, with collaboration by the British Colour Council.

THE PLANT

Name: Kristin.
Origin: Seedling.
Parentage:
*Seed parent.*—Saintpaulia "Melodie" Rhonda.

*Pollen parent.*—*Saintpaulia schumensis*×"Optimara" Georgia.
Classification: Botanic: *Saintpaulia ionantha.* Commercial: African Violet.
Form: Rosette arrangement.
Height: 7 to 8 cm.
Growth: Moderate, petioles at first upright, becoming horizontal with age.
Size: Medium to 21 cm. in diameter.
Mutation prone: None observed for lowers or foliage.
Foliage:
*Shape.*—Ovate, slight cordate base, rounded tip, slight crenate margin.
*Length.*—7 to 8 cm. on mature leaves.
*Width.*—6 to 7 cm. on mature leaves.
*Color.*—Upperside: Dark green. Underside: Pale green.
*Texture.*—Upperside: Pubescent. Underside: Puberulent.
*Ribs and veins.*—Pronounced, pinnate, red pigmented.
*Petiole.*—Flattened above, pubescent, pale green.

THE FLOWER

Blooming habit: Continuous and abundant under optimal growing conditions.
Number: Seven to nine per peduncle.
Size of flower: Each flower is approximately 3 to 4 cm. in diameter.
Color: Red-Purple, R.H.S. 67C.
Type: Single, violet-like.
Petals: Five, margins ruffled.
Texture: Smooth, slightly flexible.
Appearance: Upperside glabrous, lowerside slightly puberulent.
Peduncles: 5 to 6 cm. in height, pubescent, red pigmented.
Inflorescence: Cyme, upright, above the foliage.
Calyx: Quinquepartite, red pigmented, puberulent.
Persistence: Flowers do not drop.
Fragrance: None.

PRODUCTIVE ORGANS

Stamen: Usually two per flower.
*Anthers.*—Bright yellow, basifixed, two per filament.
*Filaments.*—c. 0.4 cm. in length.
*Pollen.*—Light yellow.
Pistils: One.

*Stigma.*—Visible and accessible, becoming swollen when receptive and exuding a droplet of clear liquid.

*Style.*—c. 0.7 cm. in length.

*Ovary.*—Superior.

I claim:

1. A new and distinct cultivar of African violet named 'Kristin', as described and illustrated, and particularly characterized by its profuse flowering, upright flower stems, compact bouquet, vigorous growth habit, flowering 11 to 12 weeks after potting and its long lasting and non-dropping flowers which gives the plant a substantially continuous beauty.

* * * * *

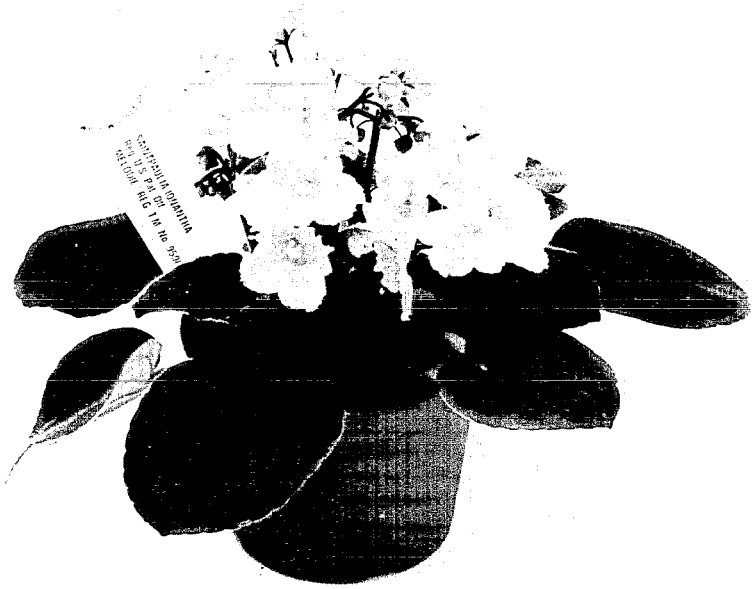
SAINTPAULIA IONANTHA
BOL. U.S. PAT. OFF.
MEDIUM REG 1 to 16 to 1950